(12) United States Patent
Bishop

(10) Patent No.: US 7,008,926 B2
(45) Date of Patent: Mar. 7, 2006

(54) BLOOD COAGULATION FACTOR XIII FOR TREATING PLATELET DISORDERS

(75) Inventor: Paul D. Bishop, Fall City, WA (US)

(73) Assignee: ZymoGenetics Inc., Seattle, WA (US)

( * ) Notice: Subject to any disclaimer, the term of this patent is extended or adjusted under 35 U.S.C. 154(b) by 258 days.

(21) Appl. No.: 10/468,111

(22) PCT Filed: Feb. 7, 2002

(86) PCT No.: PCT/US02/03770

§ 371 (c)(1),
(2), (4) Date: Aug. 15, 2003

(87) PCT Pub. No.: WO02/067981

PCT Pub. Date: Sep. 6, 2002

(65) Prior Publication Data

US 2004/0132649 A1    Jul. 8, 2004

Related U.S. Application Data

(60) Provisional application No. 60/270,479, filed on Feb. 21, 2001.

(51) Int. Cl.
*A61K 38/00*       (2006.01)

(52) U.S. Cl. .................................................... 514/12
(58) Field of Classification Search ............... 530/350; 514/12

See application file for complete search history.

(56) References Cited

U.S. PATENT DOCUMENTS 5,612,456 A  *  3/1997  Bishop et al. ............... 530/381

FOREIGN PATENT DOCUMENTS

WO         WO 93/12813      *   7/1993

OTHER PUBLICATIONS

Anwar et al., Delayed Umbilical Bleeding-A Presenting Feature for Factor XIII Deficiency: Clinical Features, Genetics, and Managment, Oediatrics, (2002), 2 Fe., 109(2), p. 1-7.*

* cited by examiner

*Primary Examiner*—Karen Cochrane Carlson
*Assistant Examiner*—Agnes Rooke
(74) *Attorney, Agent, or Firm*—Len S. Smith; Reza Green; Marc A. Bogan

(57) ABSTRACT

Use of factor XIII for treating the symptoms of thrombocytopenia. A patient having thrombocytopenia, either chemically- or metabolically induced, is treated by administering factor XIII.

7 Claims, No Drawings

BLOOD COAGULATION FACTOR XIII FOR TREATING PLATELET DISORDERS

The present application is a 35 U.S.C. 371 application of PCT/US02/03770 filed Feb. 2, 2002, which claims the benefit of U.S. Provisional Application Ser. No. 60/270,479 filed Feb. 21, 2001, both of which are incorporated by reference herein.

BACKGROUND OF THE INVENTION

Platelet disorders may cause defective formation of hemostatic plugs and bleeding because of decreased platelet numbers (thrombocytopenia) or because of decreased function despite adequate platelet numbers. Thrombocytopenia is a condition in which an individual has a platelet count below the normal range of 250,000–500,000/ml. Thrombocytopenia may stem from failed platelet production, splenic sequestration of platelets, increased platelet destruction, or use, or dilution. Regardless of cause, severe thrombocytopenia and platelet dysfunction results in a typical pattern of bleeding: multiple petechiae in the skin, often most evident on the lower legs, scattered small ecchymoses at sites of minor trauma, mucosal bleeding (epistaxis, bleeding in the gastrointestinal tract (GI) and genitalurinary tract (GU), vaginal bleeding). Heavy GI bleeding and bleeding into the central nervous system (CNS) may be life threatening. Thus, there is a need for a treatment to inhibit bleeding caused by failed platelet production, increased platelet destruction or use.

DESCRIPTION OF THE INVENTION

The present invention fills this need by administering factor XIII to patients afflicted with platelet dysfunction, or thrombocytopenia where the thrombocytopenia is caused by metabolic disease, chemical agent or radiation.

Introduction

Examples of conditions that can lead to failed platelet production are leukemia, aplastic anemia, paroxysmal nocturnal hemoglobinuria, alcohol induced thrombocytopenia, thrombocytopenia in megaloblastic anemias, human immunodeficiency virus (HIV)-associated thrombocytopenia, idiopathic thrombocytopenic purpura, and myelodysplastic syndromes. Sequestration of platelets in enlarged spleens can also cause thrombocytopenia. This is can be caused by cirrhosis with congestive splenomegaly, myelofibrosis with myeloid metaplasia, and Gaucher's disease. Pathologic destruction of platelets may also result in thrombocytopenia. This is very often caused by platelets being coated by antibodies and then being removed by mononuclear phagocytes induced by idiopathic thrombocytopenic purpura, HIV-associated thrombocytopenia, drug induced thrombocytopenia and neonatal alloimmune thrombocytopenia. Platelet destruction can also be induced by thrombin-induced platelet damage as occurs in states with intravascular coagulation such as in complications of obstetrics, metastatic malignancy, septicemia and traumatic brain damage. Platelet destruction can also be caused by acute vascular abnormalities as is often found in thrombotic thrombocytopenic purpura-hemolytic-uremic syndrome, thrombocytopenia in adult respiratory distress syndrome and severe infections with septicemia. Thrombocytopenia can also be caused by such agents as quinidine, chemotherapy drugs, quinine, heparin, radiation, nonsteroid anti-inflammatory drugs (NSAIDs) such as aspirin, ibuprofen and naproxen.

The method of the present invention provides symptomatic relief of the thrombocytopenia or platelet dysfunction by administering factor XIII. The administration of factor XIII can be applied prophylactically or at the time of a bleeding episode.

Factor XIII, also known as fibrin-stabilizing factor, circulates in the plasma at a concentration of 20 mg/ml. The protein exists in plasma as a tetramer comprised of two A subunits and two B subunits. Each subunit has a molecular weight of 83,000 Da, and the complete protein has a molecular weight of approximately 330,000 Da. Factor XIII catalyzes the cross-linkage between the γ-glutamyl and ε-lysyl groups of different fibrin strands. The catalytic activity of factor XIII resides in the A subunits. The B subunits act as carriers for the A subunits in plasma factor XIII. Recombinant factor XIII can be produced according to the process described in European Patent No. 0 268 772 B1. The level of factor XIII in the plasma can be increased by administering a factor XIII concentrate derived from human placenta called FIBROGAMMIN® (Aventis Corp.) or by administration of recombinant factor XIII. When recombinant factor XIII is used, only the '$A_2$' homodimer is generally administered without the '$B_2$' subunit.

Administration of factor XIII to a subject is generally done intravenously. When administering therapeutic proteins by injection, the administration may be by continuous infusion or by single or multiple boluses. A pharmaceutical composition comprising factor XIII can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. A suitable pharmaceutical composition of factor XIII will contain 1mM EDTA, 10mM Glycine, 2% sucrose in water. An alternative formulation will be a factor XIII composition containing 20 mM histidine, 3% wt/volume sucrose, 2 mM glycine and 0.01% wt/vol. polysorbate, pH 8. The concentration of factor XIII should preferably be 1–10 mg/mL, more preferably about 5 mg/mL.

Other suitable carriers are well known to those in the art. See, for example, Gennaro (ed.), *Remington's Pharmaceutical Sciences*, 19th Edition (Mack Publishing Company 1995).

Administration of Factor XIII

Factor XIII can be administered intravenously, intramuscularly or subcutaneously to treat platelet dysfunction or thrombocytopenia caused by metabolic disease, chemical agents or radiation. The levels of factor XIII in an individual can be determined by assays well known in the art such as the BERICHROM® F XIII assay (Dade Behring Marburgh GmbH, Marburg, Germany). The normal adult has an average of about 45 ml of plasma per kg of body weight. Each liter of blood has 1000 units (U) of factor XIII. The amount of factor XIII administered should be enough to bring an individual's level of factor XIII in the plasma to at least 100% of normal plasma or preferably 1–5% above normal. A dose of 0.45 U/kg would raise the level of factor XIII by about 1% compared to normal. One unit of factor XIII is about 10 μg of recombinant factor XIII, which contains only the dimerized A subunit. Thus, to raise the level of factor XIII by 1%, one would administer about 4.5 μg of the A2 subunit per kilogram weight of the individual. So to raise the level 30% of normal, one would administer 13.5 U/kg. For a 75 kg individual this would be about 1,012.5 U. Some patients may have consumptive coagulopathies that involve factor XIII losses. In such cases, a higher dosing (e.g., 1–2U/kg-%) or multiple dosing of factor XIII (e.g., 1–2U/kg-%-day) may be required.

What is claimed is:

1. A method for treating chemically-induced or metabolically induced thrombocytopenia in an individual comprising administering to the individual a therapeutically effective amount of factor XIII.

2. The method of claim 1, wherein the thrombocytopenia is caused by a condition selected from the group consisting of leukemia, aplastic anemia, megaloblastic anemia, human immunodeficiency virus-associated thrombocytopenia, idiopathic thrombocytopenic purpura, and myelodysplastic syndromes.

3. The method of claim 1, wherein the thrombocytopenia is a condition elected from the group consisting of cirrhosis with congestive splenomegaly, myelofibrosis with myeloid metaplasia, and Gaucher's disease.

4. The method of claim 1, wherein the thrombocytopenia is caused by alcohol, quinidine, chemotherapeutic drugs, quinine, heparin, radiation, or nonsteroidal anti-inflammatory drugs.

5. The method of claim 1, wherein the factor XIII is administered during a bleeding episode.

6. A method for treating platelet dysfunction in an individual comprising administering to the individual a therapeutically effective amount of factor XIII.

7. The method of claim 6, wherein the factor XIII is administered during a bleeding episode.

* * * * *